Figure 1:
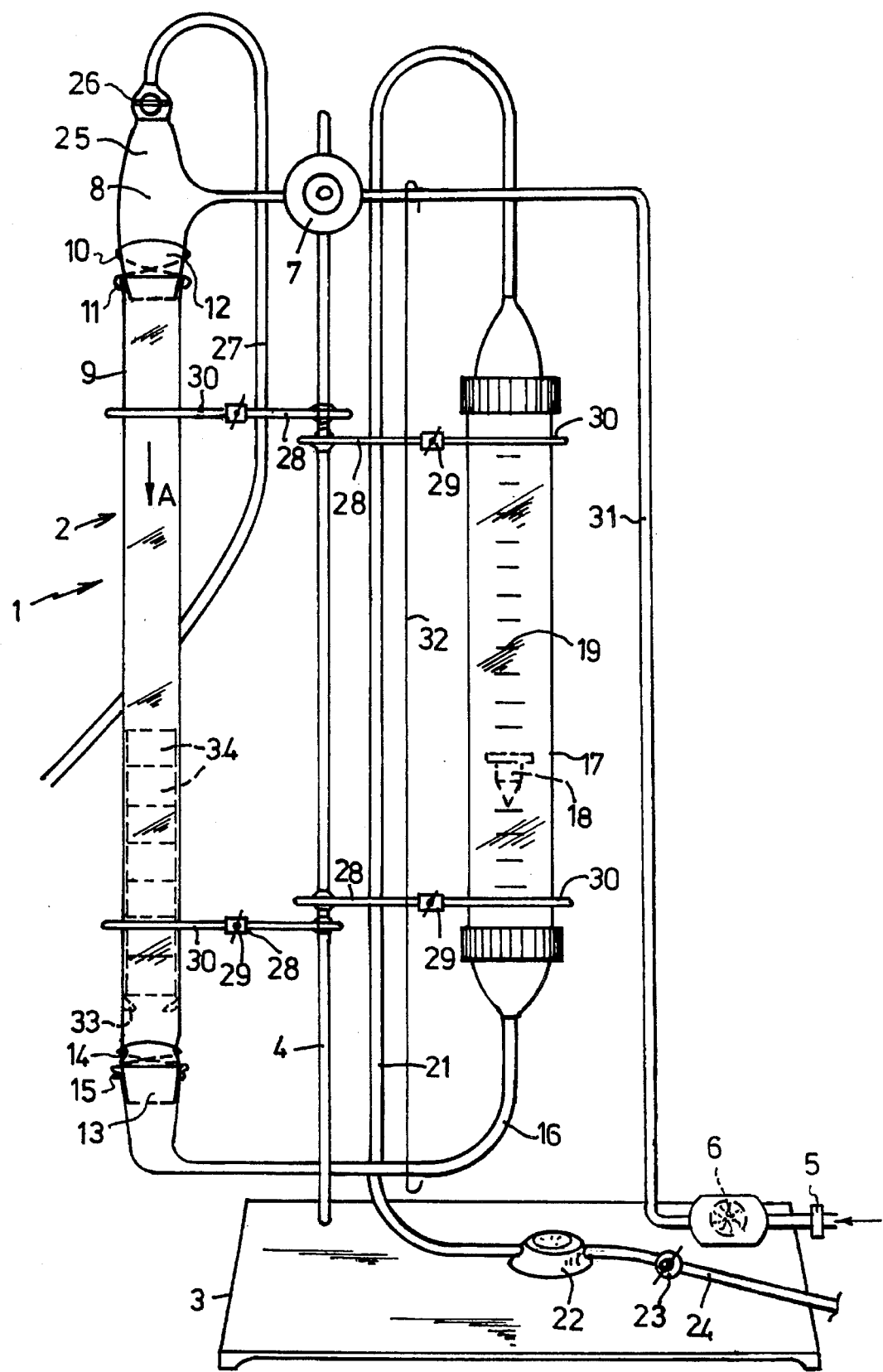

United States Patent [19]

Dirk

[11] Patent Number: 5,488,856
[45] Date of Patent: Feb. 6, 1996

[54] MONITOR FOR GROWTH AND DEPOSIT

[75] Inventor: Van Der Kooij Dirk, Nieuwegein, Netherlands

[73] Assignee: Kiwa N.V., Nieuwegein, Netherlands

[21] Appl. No.: 178,307

[22] PCT Filed: Jul. 13, 1992

[86] PCT No.: PCT/NL92/00128

§ 371 Date: Jun. 2, 1994

§ 102(e) Date: Jun. 2, 1994

[87] PCT Pub. No.: WO93/01497

PCT Pub. Date: Jan. 21, 1993

[30] Foreign Application Priority Data

Jul. 11, 1991 [NL] Netherlands .............. 9101221

[51] Int. Cl.⁶ .............. G01N 5/00; C12M 3/00; G01M 17/00
[52] U.S. Cl. .............. 73/61.62; 73/61.41; 73/866.5
[58] Field of Search .............. 73/61.62, 61.63, 73/61.41, 61.42, 866.5

[56] References Cited

U.S. PATENT DOCUMENTS

| | | | |
|---|---|---|---|
| 3,174,332 | 3/1965 | Echtler, Jr. et al. .............. | 73/86 |
| 3,198,005 | 8/1965 | Wolfson .............. | 73/53 |
| 3,392,575 | 7/1968 | Galler .............. | 73/61.2 |
| 4,466,277 | 8/1984 | Baier et al. .............. | 73/61.2 |
| 4,631,961 | 12/1986 | Yohe .............. | 73/866.5 |
| 5,299,449 | 4/1994 | Hardy et al. .............. | 73/61.62 |
| 5,376,548 | 12/1994 | Matsuo et al. .............. | 435/284 |

FOREIGN PATENT DOCUMENTS

| | | |
|---|---|---|
| 0327386 | 8/1989 | European Pat. Off. . |
| 2619979 | 3/1978 | Germany . |

OTHER PUBLICATIONS

US, H, 831 (Salanitro) 2 Oct. 1990 Statuatory Invention Registration.

*Primary Examiner*—Hezron E. Williams
*Assistant Examiner*—J. David Wiggins
*Attorney, Agent, or Firm*—Ladas & Parry

[57] ABSTRACT

A method for monitoring the formation of biofilm on surfaces which are exposed to a flowpath of liquid essentially containing water includes flowing a liquid along the flowpath only once without being circulated through a tube section, through and along a series of sample tube pieces removably placed within the tube section, successively removing the sample tube pieces without replacement each time after a period of flow elapses and testing the sample pieces removed to determine the biofilm formation thereon. The tube section is arranged essentially vertically, and the flow through the tube section is downwardly directed, the uppermost sample tube pieces being removed in succession after each time period of flow exposure.

24 Claims, 1 Drawing Sheet

MONITOR FOR GROWTH AND DEPOSIT

The invention relates to a monitor for surveying the formation of deposit and/or growth, being especially but not exclusively a biofilm monitor, comprising a deposit reactor as well as a method for the use of this deposit monitor.

When drinking water flows through a mains, a small layer of bacteriological material, also called biofilm, will be deposited on the inner surface of the mains. The formation of this biofilm in systems for the distribution of drinking-water and in drinking-water installations is undesirable for technical, aesthetic and hygienic reasons. Research has shown that due to the formation of biofilm on the mains surface, the hydraulic resistance thereof can increase noticeably. In addition the biofilm can form a breeding ground for animal organisms of which some can be seen with the naked eye, such as the water sow bug (Asellus). Perhaps the hygienic aspect is even more important. Some types of bacteria which grow in the biofilm have pathogenic properties such as the Legionella bacteria, the perpetrator of the so-called Legionnaire's disease and also representatives of the Aeromonas family, which can cause diarrhoea. Growth of bacteria of the coli (bacillus) type in the biofilm can result in the water not complying with the legal requirements (absence of bacteria of the coli type in 100 ml drinking-water).

The formation of a biofilm is dependant upon the nature and the concentration of degradable matter ("sources of energy") in drinking-water. These sources of energy include organic and also certain inorganic compounds. There are however more factors which presumably play a part. The following can be mentioned: the type of material from which the mains are made (the one material restrains the growth of bacteria to a larger extent than the other), also the age of the mains material, the water temperature, the flow velocity and the occurrence of physicochemical processes such as adsorption and sedimentation.

In order to study the effect of certain circumstances on the formation of biofilm and/or to study the effect of the formation of biofilm on the quality of the drinking-water, use is made of so-called biofilm reactors. An important example of such a biofilm reactor is the "Roto Torque (RT)" reactor, which consists mainly of a stationary and an uprightly positioned cylinder sleeve formed by a tube section of a mains and a massive rotatable cylindrical block positioned therein. The liquid sample is introduced in a continuous fashion, and is then thoroughly mixed with previously introduced liquid by virtue of continuous rotation of the rotor and drained continuously, the residence time of the liquid particles in the reactor amounting to approximately 10 minutes. The Roto Torque reactor can, because of its constant mixing, be classed under the so-called CFSTR's (Continuous Flow Stirred Tank Reactor). A torque meter is connected to the rotor of the Roto Torque, by which the torque required for maintaining a certain speed of revolution is determined. With the development of biofilm on the inner surface of the sleeve the shear stress along the surface increases, as a result of which a larger torque will be necessary. The increase of the required torque is thus a measure for the formation of biofilm, which in this way is monitored indirectly.

In order to come as close as possible to real cicumstances several Roto Torque's can be placed in series in a Roto Torque System (RTS). This way an attempt is made to determine the influence of concentration gradients.

The Roto Torque reactor and the Roto Torque System are not always suitable for studying biofilm formation. In the first place the construction forms a hindrance: because of the implementation of a rotor set up inside the test pipe the latter will have to have a considerable diameter, for example 15 cm. Consequently this reactor is indeed suitable for tests on mains pipes but not for tests with service pipes. Secondly, the results will not always be exact and reliable due to the aforementioned indirect method of measuring the formation of biofilm. Thirdly it is not possible to analyse the change in the course of time in physical and biological properties of the biofilm as opposed to changes in weight by using the Roto Torque. This can only be done with several Roto Torques, in the above mentioned RTS; this system is however bulky, difficult to handle and expensive.

It was found that there is a growing demand for a method by which the formation of deposits, in particular biofilm, on surfaces of all sorts of pipes, under circumstances which come as close as possible to reality, can be monitored in a simple and cheap manner. The invention thus provides a method for monitoring the formation of deposits on surfaces which are exposed to a liquid containing essentially water, wherein the liquid particles are carried once only without circulation through a tube section through and/or along a series of removable sample pieces placed within the tube section and against one another, the sample pieces being successively removed each time after a period of flow without being replaced and then treated to determine the deposit formation thereon.

By means of the method according to the invention a section of a tube, a sample piece, will be removed at intervals after it has been exposed for a time to real circumstances, that is to say non-circular flow, in order to subject the depository film which has developed thereon to closer investigation. Withdrawing the sample pieces at intervals makes it possible to exactly determine the influence of time on a variety of matters. Placing the sample pieces inside a tube section also has the advantage that the sample pieces only perform the function of providing a surface for deposit formation, so that after the sample pieces have been withdrawn, they do not have to be replaced, which considerably simplifies the tests. At the same time the risk that the surface of the sample pieces, on which deposits, in particular biofilm will be or have been developed, is touched, is minimized.

The sample pieces can be tubular, cruciform or star-shaped. In the case of tubular sample pieces, it is beneficial if they are provided with spacer means on their outer surface so that they can be centered relative to the tube section and to one another. The spacer means can be formed as studs, for example three studs spaced over the circumference of the tube. In the cruciform or star-shaped embodiment centering can already have been provided by, for example, the radially projecting stems.

It is preferable to arrange the tube section in an essentially vertical position and the flow is carried downstream through it, the uppermost sample piece being removed each time. Due to this the effects of gravity are as far as possible distributed uniformly over the flow area and at the same time arranged in such a way that just a minimal space is taken up. This is of particular advantage if the tube section is connected to the public water mains and the flow takes place with water out of it. In this way deposit or biofilm specimens can be taken in various places, also outside laboratories, the small space usage being obviously very practical.

According to a further preferential implementation of the method of the invention the liquid is carried through a number of serially placed tube sections with sample pieces serially arranged therein, said tube sections being connected by upward flow pipe sections. In this way the test can be carried out over a very long period of time, without it being repeatedly interfered with, while the use of space is limited as far as possible.

In order to approach real circumstances as far as possible the flow velocity is set in such a manner that the time of contact of the liquid particles with a sample piece is in the order of 0.1 seconds and/or that it is in the order of 0.2 m/sec., which more or less corresponds to the flow velocity of the Dutch water mains system.

The invention relates moreover to an apparatus which is suitable for implementing the method according to the invention. Thus the invention provides an apparatus for monitoring the formation of deposit, such as biofilm, on surfaces which are exposed to a liquid containing essentially water, comprising a tube system with an inlet and an outlet for conducting the liquid, the tube system comprising at least one tube section with a series of sample tubes arranged against one another and in flow direction and means for affording access to the tube section in order to remove and/or place the sample pieces, it being preferable that the tube section extends essentially in a vertical direction and is provided with means for supporting a stack of sample pieces.

It is observed that a biofilm reactor for studying formation of biofilm in heat exchanger pipes is known, being equipped for the aforementioned circulation flow (CFSTR) and having a horizontal tube section, which itself comprises a series of sample tubes pressed together against one another. These sample tubes have to be replaced when removed, which is of particular inconvenience with the last sample tubes, due to the chances of touching the developed biofilm being considerable.

It is preferable that the apparatus comprises a number of serially connected separately accessible tube sections provided with sample pieces. The separate accessibility of the tube sections limits the interference necessary each time on of the test pieces is removed, which is advantageous in view of the likelihood of mistakes occurring and in view of the time required for the tests.

It is furthermore preferable that a flow meter be included into the tube system, downstream from the tube section(s), the flow meter essentially extending vertically. In this way the setting of the flow rate during the experiment can be monitored without noticeably enlarging the space usage.

Preferably means are provided for connecting the inlet of the tube system with the public drinking-water supply so that the apparatus can be linked at random places to the local drinking-water supply in order to use drinking-water as a testing liquid for tests on deposit formation. In addition it is convenient if a reducing valve is disposed in the tube system, above the tube section(s), so that pressure fluctuations in the mains supply are levelled out.

It is moreover convenient if the apparatus is provided with means for removing air from the tube system. By this, air which may have entered the tube system during the removal of a sample piece and which might disturb a normal correct flow, can be expelled.

It is beneficial especially with respect to the desired mobility of the apparatus according to the invention, and particularly if the connection is desired at random points on the water mains supply, if the apparatus is constructed as compact and maneuverable as possible, for which support means are provided for collectively supporting the component parts of the apparatus.

The apparatus will be explained in more detail by means of a purely exemplary embodiment of the apparatus according to the invention, and also be means of the use thereof.

FIG. 1 shows a biofilm monitor 1, comprising a tube system 2 kept in place and upright by means of brackets 30, bracket clips 29, transverse rods 28, stand 4 and supporting base 3.

The first portion of the tube system 2 comprises successively a schematically shown connecting piece 5 for connecting to a (not represented) tap of a water mains, an optional pump 6, in the unlikely event of there being insufficient water pressure (local circumstances), and a pipe portion 31 leading to a reducing valve 7, which is used to level out pressure fluctuations in the water supply. The following portion of the tube system 2 comprises a T-shaped length of pipe 8, closed off on the top 25 by an air release valve 26, which can shut off a ventilation tube 27 and is connected to a test tube section 9 on the lower side 12. The test tube section 9 is made of transparent material such as glass and is provided on its upper end with a flange assembly 11, which is connected with the widened lower edge 12 of the T-shaped length of pipe 8 by means of spring-clip 10 in a usual fashion the flange assembly being releasable, yet still sufficiently liquid-proof. The test tube section 9 is on its lower edge furthermore provided with a widened part 13, which in turn is connected in the usual way with the help of spring-clip 14 to flange assembly 13 of the connecting tube 16, which forms the connection between the test tube section 9 and a flow meter 17. The vertically positioned, transparent flow meter 17 is provided with an indicator 18 and a scale division 19, the position of the indicator being determined by gravity and by the strength of the upstream flow through the flow meter and, in connection with the scale division 19, giving an indication as to the flow rate. The flow meter is connected through tube 20, 21 to a water-meter 22 placed on the base 3 and a valve 23 also placed on base 3 downstream from there. Downstream from the valve 23 there is a drainage end 24 with which water can be drained off into the sewers or, local regulations permitting, into the public water mains.

The test tube section 9 is provided with supports 33 on its inner surface, on which a stack of tube pieces 34 is stacked, fitting loosely into the test tube section 9. The tube pieces 34 can be made of the same material as the conduit to be tested, in other words made of teflon, PE, PVC, copper, steel and/or a material suitable for investigating the formation of biofilm, such as glass.

In an experiment with aforementioned biofilm monitor the inner diameter and the length of the test tube 9 were 25 and 700 mm respectively, tube pieces 34 made of glass and teflon being used in various experiments. The diameter and the length of the tube pieces 34 measured 15 and 15 mm respectively. In one of the experiments forty tube pieces 34 were stacked in the test tube section 9. The diameter of the tube pieces 34 was such that flow along their outer surface and thereby biofilm formation thereon occurred as well. It was seen to, that during the flow light conditions around the tube pieces were maintained as dark as possible.

In an other experiment several test tube sections 9 were connected serially and joined to one another through tube portions which extended from the lower side of a test tube section to the upper side of the following test tube section located downstream from there.

With the help of the flow meter 17 and the valve 23 the correct flow rate was set, whereby a flow velocity of 0.2 meters per section was achieved. This flow velocity corresponds with that of the water in the Dutch water mains. It appeared that no noticeable concentration gradient occurred, probably as a result of the short time of contact, a beneficial outcome thereof being that the formation of biofilm on the tubes was at any rate almost independent of the location. In one experiment with several test tube sections, each time the uppermost tube pieces were simultaneously removed and no appreciable differences in biofilm formation between them were ascertained. The point seemed to be not to set the throughput speed at too low a rate. It was to be expected that, as a rate of 0.2 meter/hour, corresponding to the flow velocity during the preparation of drinking-water, no useful results would be obtained because then a noticeable concentration gradient could occur.

Periodically, for example once a day, once per week or every two weeks, and after the inlet was shut off and the length of pipe 8 had been disconnected from the test tube section, the top tube piece was taken vertically out of the test tube section(s) in a restrained way, with the help of the stainless steel rod 32, with no notable damaging of the biofilm. Water was allowed to subside (slowly) to the bottom of the tube piece to be withdrawn, in order to prevent biofilm—which could loosely coat the surface of the test tube—being washed off as a result of the relative flow generated by lifting the tube piece up through the water during removal of the tube piece. With the help of bacteriological and chemical determinants the amount of biofilm on the tube pieces was measured and converted to an amount per square centimeter. By means of various culture media or, otherwise, a direct counting method the number of cultivatable bacteria per tube piece was determined. Furthermore the content of adenosine triphosphate (ATP) was determined as an indicator for the biomass and the bio-activity. Experiments were also carried out, whereby the contents of iron, manganese and calcium were determined by means of the monitor according to the invention. It appeared that whilst the water to be tested flowed through the test tube section the compounds in question were also deposited (because of insufficient removal) on the surfaces of the sample pieces.

The quantity and the speed of deposit form an indication as to the water composition and/or the working of water purification with respect to the above mentioned compounds. In one case the water appeared to cause calcification. The reason for this appeared to be the occurrence of post-crystalization after softening treatment had taken place during purification. A re-softening of this kind is undesirable in the water mains in connection with the incidence of blockages in the pipes/apparatus.

Measurements of other anorganic compounds (such as: aluminium, phosphate, silicate) as well as of organic compounds can also be carried out in order to gain an impression of the deposits which occur from out of the water onto the surface.

After removing in each case the uppermost tube piece, the length of pipe 8 was again fitted into the upper end of the test tube section 9 and the tube system 2 was filled with water. Air collected in the upper end of the length of pipe 8 was expelled by opening valve 26 and causing underpressure in the conduit 27. After air has been expelled from the length of pipe 8 the valve 26 was closed again and the system according to the invention could again be put into operation. It is goes without saying that it was not necessary to re-set each time, because it was usually sufficient to reproduce the position of the supply tap.

With the results of several tens of sample tube pieces 34 removed at intervals the ATP content as a time function could be plotted out. The rate of biofilm formation (BFR, pg ATP/cm$^2$ per day) could be calculated from the graph gradient and the biofilm formation potential (BFP, pg ATP/cm$^2$) of the examined water could be calculated from the maximum ATP level.

It also seems feasible to arrange the column(s) of sample tube pieces using tube pieces made of a variety of materials if the length of the test tube section is adequate enough. In this way a tube piece column can be composed of groups of, for example, three pieces each of for instance PVC, PE and copper respectively, and then, one group at a time, the group which is at that moment uppermost is removed. Due to the almost complete absence of a concentration gradient, the biofilm formation on the tube pieces of one group can be mutually compared so that an impression of the (pipe) material for biofilm formation in a certain type of water is gained.

I claim:

1. Method for monitoring the formation of deposits on surfaces which are exposed to a flowpath of liquid essentially containing water, said method comprising flowing a liquid along a flowpath once only without being circulated through and along a tube section, the flowpath including a series of sample pieces having surfaces for deposit formation thereon removably placed within the tube section and abutted against each other with the geometrical axis of each piece oriented along the liquid flowpath, successively removing without replacement said sample pieces each time after another time period of flow exposure elapses and testing said sample pieces removed to determine the existence, thickness, type or composition of deposit formation thereon.

2. Method according to claim 1, wherein the sample pieces are provided with spacer means for positioning relative to the inner diameter surface of the tube section and for positioning and accurate centering of the sample pieces relative to one another.

3. Method according to claim 2, wherein the spacer means are provided on the outer diameter surface of the sample pieces.

4. Method according to claim 1, wherein the sample pieces are essentially star-shaped or cruciform-shaped.

5. Method according to claim 1, wherein the sample pieces are essentially tubular-shaped.

6. Method according to claim 1, wherein the tube section is arranged essentially vertically, and the flow through said tube section is downward directed, the upstream sample piece or the upstream sample pieces respectively being removed in succession after each time period of flow exposure.

7. Method according to claim 6, wherein the liquid is passed through a number of serially placed tube sections each with a set of sample pieces arranged in a separate series, with each of the different tube sections connected by upward flow pipes.

8. Method according to claim 1, wherein the tube section is connected to the public water mains, the flow through said tube section taking place with water from the public water supply.

9. Method according to claim 1, whereby the formation and rate of growth of biofilm on the sample pieces is monitored according to film thickness, biomass type, biomass activity and composition.

10. Method according to claim 1, whereby the formation of iron, manganese and/or calcium compounds on the sample pieces is monitored.

11. Method according to claim 1, wherein the flow velocity is set in such a way that the time of contact of the liquid particles with a sample piece is approximately 0.1 seconds.

12. Method according to claim 1, wherein the flow velocity is set to approximately 0.2 m/sec. corresponding to that in the Netherlands public water mains.

13. Apparatus for monitoring the formation of deposit, such as biofilm, on surfaces which are exposed to a flowpath of liquid containing essentially water, said apparatus comprising a tube system provided with an inlet and an outlet for conducting the liquid, the tube system comprising a flowpath of at least one tube section with a series of sample pieces inserted inside, arranged in abutment against each other and each sample piece having its geometrical axis oriented along the liquid flowpath within said tube section and means for affording access to the tube section in order to remove and/or position any of the sample pieces disposed within said tube section.

14. Apparatus according to claim 13, wherein the sample pieces are provided with spacer means for positioning relative to the inner diameter surface of the tube section and for positioning and accurate centering of the sample pieces relative to one another.

15. Apparatus according to claim 14, wherein the spacer means are provided on the outer diameter surface of the sample pieces.

16. Apparatus according to claim 13 in which the sample pieces are cruciform-shaped or star-shaped.

17. Apparatus according to claim 13 in which the sample pieces are essentially tubular-shaped.

18. Apparatus according to claim 13, in which the tube section extends essentially vertically and is provided with means for supporting a stack of sample pieces.

19. Apparatus according to claim 13, comprising a number of serially connected separately accessible tube sections each provided with a series set of sample pieces.

20. Apparatus according to claim 13, comprising a flow meter incorporated in the tube system, at a position in the flowpath downstream from the tube section and the sample pieces, and having an orientation extending essentially vertically.

21. Apparatus according to claim 13, comprising means for connecting the inlet of the tube system to the public drinking-water supply.

22. Apparatus according to claim 21, comprising a reducing valve incorporated in the tube system at a position in the flowpath downstream from the tube section and the sample pieces.

23. Apparatus according to claim 13, comprising means for removing air from the liquid flowpath within the tube system.

24. Apparatus according to claim 13, further comprising support means for supporting the tube system.

* * * * *